United States Patent [19]

Erekson et al.

[11] Patent Number: 5,043,505

[45] Date of Patent: * Aug. 27, 1991

[54] OXIDATIVE COUPLING OF ALIPHATIC AND ALICYCLIC COMPOUNDS AND MIXED BASIC METAL OXIDE CATALYST THEREFORE

[75] Inventors: Erek J. Erekson, LaGrange; Anthony L. Lee, Glen Ellyn; S. Peter Barone, Hoffman Estates; Irvine J. Solomon, Highland Park, all of Ill.

[73] Assignee: Institute of Gas Technology, Chicago, Ill.

[*] Notice: The portion of the term of this patent subsequent to May 2, 2006 has been disclaimed.

[21] Appl. No.: 517,068

[22] Filed: May 7, 1990

Related U.S. Application Data

[63] Continuation-in-part of Ser. No. 274,415, Nov. 21, 1988, Pat. No. 4,935,572, Ser. No. 359,207, May 31, 1989, Pat. No. 4,945,078, and Ser. No. 359,500, May 31, 1989, Pat. No. 4,956,327, said Ser. No. 274,415, is a continuation-in-part of Ser. No. 271,808, Mar. 28, 1988, Pat. No. 4,826,796, said Ser. No. 359,207, is a continuation-in-part of Ser. No. 274,415, Nov. 21, 1988, Ser. No. 274,499, Nov. 21, 1988, Pat. No. 4,950,830, and Ser. No. 274,454, Nov. 21, 1988, Pat. No. 4,950,827, each is a continuation-in-part of Ser. No. 172,808, Mar. 28, 1988, Pat. No. 4,826,796.

[51] Int. Cl.$^5$ .......................... C07C 2/00; B01J 21/02

[52] U.S. Cl. .................................. 585/415; 502/202; 502/243; 502/303; 502/341; 502/342; 502/344; 585/943; 585/636; 585/500; 585/921; 585/926; 585/417; 585/654; 585/700

[58] Field of Search ............... 585/415, 500, 541, 654, 585/700, 721, 926, 943; 502/202, 243, 303, 341, 342, 344

[56] References Cited

U.S. PATENT DOCUMENTS

| | | | |
|---|---|---|---|
| 4,544,785 | 10/1985 | Withers et al. | 585/500 |
| 4,560,804 | 12/1985 | Yeh et al. | 585/408 |
| 4,571,290 | 2/1986 | Ward et al. | 204/157.69 |
| 4,826,796 | 5/1989 | Erekson et al. | 502/202 |
| 4,935,572 | 6/1990 | Erekson et al. | 585/415 |
| 4,945,078 | 7/1990 | Erekson et al. | 502/202 |
| 4,956,327 | 9/1990 | Erekson et al. | 502/216 |

FOREIGN PATENT DOCUMENTS 0104507 9/1983 European Pat. Off.
0177327 10/1985 European Pat. Off.

*Primary Examiner*—Asok Pal
*Attorney, Agent, or Firm*—Thomas W. Speckman; Douglas H. Pauley

[57] ABSTRACT

A catalytic process for gas phase oxidative coupling of aliphatic and alicyclic hydrocarbon compounds to produce higher molecular weight hydrocarbon compounds, the catalyst being a mixed basic metal oxide or sulfide catalyst. One preferred mixed basic metal oxide catalyst is boron/alkali metal promoted metal oxide.

44 Claims, No Drawings

OXIDATIVE COUPLING OF ALIPHATIC AND ALICYCLIC COMPOUNDS AND MIXED BASIC METAL OXIDE CATALYST THEREFORE

CROSS-REFERENCE TO RELATED APPLICATIONS

This application is:

a continuation-in-part of copending U.S. patent application Ser. No. 07/274,415, now U.S. Pat. No. 4,935,572 filed Nov. 21, 1988 as a continuation-in-part of U.S. patent application Ser. No. 07/172,808, filed Mar. 28, 1988, now U.S. Pat. No. 4,826,796;

a continuation-in-part of copending U.S. patent application Ser. No. 07/359,207, now U.S. Pat. No. 4,945,078 filed May 31, 1989 as a continuation-in-part of U.S. patent applications, Ser. Nos. 07/274,415, now U.S. Pat. No. 4,935,572; 07/274,499, now U.S. Pat. No. 4,950,830; and 07/274,454, now U.S. Pat. No. 4,450,8 , all filed Nov. 21, 1988 as a continuation-in-part of U.S. patent application, Ser. No. 07/172,808, filed March 28, 1988, now U.S. Pat. No. 4,826,796; and a continuation-in-part of copending U.S. patent application, Ser. No. 07/359,500, now U.S. Pat. No. 4,956,327 filed May 31, 1989.

BACKGROUND OF THE INVENTION
1. Field of the Invention

This invention relates to production of higher hydrocarbons by oxidative coupling of aliphatic and alicyclic compounds using mixed basic metal oxide and sulfide catalysts. Reaction of aliphatic and alicyclic compounds with oxygen in the presence of mixed basic metal oxide and sulfide catalyst in accordance with the process of this invention results in high conversion to longer chain products.

2. Description of the Prior Art

Methane is currently available in large quantities from natural gas, anaerobic digestion of organic material, and chemical processing sources. However, use of methane as a chemical feedstock has been limited due to its high stability. It has been highly desirable to develop a catalyst for such reactions to enable operation under milder conditions with greater control over thermodynamic and kinetic processes as well as provide product selectivity and high reaction rate.

Oxidative coupling of methane to form higher hydrocarbons has been shown to be effected over a number of metal oxides, but yields of desired products have been low, as discussed by Keller, G. E. and M. M. Bhasin, J. of Catalysis 73, 9-19 (1982). Sodium and lead on alumina has been found to catalyze the formation of ethane and ethylene from methane, as disclosed in Hinsen, W. and M. Baerns, Chem.-Ztg., 107, 223-226 (1983) and Hinsen, W., W. Bytyn and M. Baerns, Proc. 8th Int. Congr. Catal., Berlin, III 581-592 (1984). Several U.S. patents teach a series of supported metal oxides which while effective for the conversion of methane to ethane and ethylene, are based on reducible metal oxides and used in a stoichiometric fashion by alternately exposing them to an oxidizing atmosphere and then to methane in the absence of oxygen. U.S. Pat. Nos. 4,443,644; 4,443,645; 4,443,646; 4,443,647; 4,443,648; 4,443,649; 4,444,984, 4,499,322; 4,499,323; 4,499,324; and 4,523,049.

Later work has demonstrated that magnesium oxide and calcium oxide, when promoted with alkali metal salts, are active for oxidative coupling of methane to ethane and ethylene in the presence of oxygen. See Kimble, James B. and John H. Kolts, "Oxidative Coupling of Methane to Higher Hydrocarbons", Energy Progress, Vol. 6, p. 227 (1986); Driscoll, D. J., W. M. Martir, J. Wang and J. H. Lunsford, J. Am. Chem. Soc. 107, 58-63 (1985); and Ito, T., J. Wang, C. Lin and J. H. Lunsford, J. Am. Chem. Soc. 107, 5062-64 (1985). These later catalysts have the advantage of operating continuously, not requiring regeneration or pretreatment.

Borates and boron compounds have been used in partial oxidation of hydrocarbons, such as boric acid to oxidize long chain normal paraffins in the liquid phase (Illingworth, G. F. and G. W. Lester, ACS Petroleum Division Preprints, 12, No. 3, 161 (1967)) and oxidation of n-dodecane in the liquid phase to the corresponding alcohol (Lee, K. W., M. J. Choi, S. B. Kim and C. S. Choi, Ind. Eng. Chem. Res. 26, 1951 (1987)). Boric acid has been used by coating reactor walls in the combustion of methane to eliminate free radical destruction at temperatures of less than 513° C. (Kegeyan, E. M., I. S. Vardanyan and A. B. Nalbandyan, Kinetics and Catalysis 17, No. 4,749-754 and No. 4,755-759 (1976)). A catalytic process for production of higher molecular weight hydrocarbons from lower molecular weight hydrocarbons using a metal containing catalyst of single metal carbides, nitrides, borides or oxides, high temperatures, and high gas hourly space velocity in a pyrolysis process not requiring oxygen is taught by U.S. Pat. Nos. 4,704,487; 4,704,488; and 4,704,493.

SUMMARY OF THE INVENTION

This invention provides a catalytic process for oxidative coupling of aliphatic and alicyclic compounds to produce higher molecular weight hydrocarbons. Catalysts used in the process of this invention are described in U.S. patent applications: Ser. No. 07/172,808, filed Mar. 28, 1988, now U.S. Pat. No. 4,826,796; Ser. No. 07/274,415, filed Nov. 21, 1988, now U.S. Pat. No. 4,935,572; Ser. No. 07/359,207, filed May 31, 1989, now U.S. Pat. No. 4,945,078; and Ser. No. 07/359,500, filed May 31, 1989, now U.S. Pat. No. 4,956,327. Oxidative coupling of aliphatic and alicyclic hydrocarbons with aliphatic and alicyclic substituted aromatic hydrocarbons using these catalysts is described in U.S. patent applications: Ser. No. 07/274,454, filed Nov. 21, 1988, now U.S. Pat. No. 4,950,827, and Ser. No. 07/359,500, filed May 31, 1989, now U.S. Pat. No. 4,956,327. Oxidative coupling of methane using these catalysts is described in U.S. patent applications: Ser. No. 07/274,415, filed Nov. 21, 1988, now U.S. Pat. No. 4,935,572; Ser. No. 07/359,207, filed May 31, 1989, now U.S. Pat. No. 4,956,327; and Ser. No. 07/359,500, filed May 31, 1989, now allowed. The disclosures of these prior applications are incorporated herein in their entireties.

The reaction of aliphatic and alicyclic compounds with oxygen is conducted in the presence of a mixed basic metal oxide or sulfide catalyst at elevated temperature to result in high conversion to longer chain products. The mixed basic metal catalyst used in the process of oxidative coupling of aliphatic and alicyclic compounds has the formula:

$$xA \cdot yB \cdot zC \cdot qD$$

wherein

A is an alkali metal selected from lithium, sodium, potassium, rubidium, cesium and mixtures thereof;

B is selected from the group consisting of;

a cation which has an ionization state 1 greater than the ionization state of C wherein B is selected from scandium, yttrium, lanthanum, actinium, aluminum, boron, and mixtures thereof, preferably boron, aluminum, yttrium, and lanthanum when C is selected from beryllium, magnesium, calcium, strontium, barium, radium, zinc cadmium mercury and mixtures thereof, preferably magnesium, calcium, barium and zinc; and B is selected from titanium, zirconium, hafnium, silicon and mixtures thereof, when C is selected from scandium, yttrium, lanthanum, actinium, aluminum, boron and mixtures thereof, preferably boron, aluminum, yttrium, and lanthanum; and a cation which has an ionization state 2 and 3 greater than the ionization state of C wherein B is selected from hafnium, tantalum, niobium, vanadium and mixtures thereof; C is selected from magnesium, calcium, strontium, barium, and mixtures thereof;

D is selected from oxygen, and sulfur;

x and y are in the mole fractions of z such that when $z=1$ then $x=0.001$ to 0.25, preferably 0.05 to 0.15 and $y=0.001$ to 0.25, preferably 0.002 to 0.20; and q is a number necessary to maintain charge balance with D.

The mixed basic metal oxide catalyst of this invention wherein B is a cation having an ionization state 1 greater than the ionization state of C used in the process of oxidative coupling of aliphatic and alicyclic compounds has the formula:

$$xA.yB.zC.qO$$

wherein

A is an alkali metal selected from lithium, sodium, potassium, rubidium, cesium and mixtures thereof;

B is a cation which has an ionization state 1 greater than the ionization state of C;

B is selected from scandium, yttrium, lanthanum, actinium, aluminum, boron, and mixtures thereof, preferably boron, aluminum, yttrium, and lanthanum when C is selected from beryllium; magnesium; calcium; strontium, barium, radium, zinc, cadmium, mercury and mixtures thereof, preferably magnesium, calcium, barium and zinc, and B is selected from titanium, zirconium, hafnium, silicon and mixtures thereof, when C is selected from scandium, yttrium, lanthanum, actinium, aluminum, boron and mixtures thereof, preferably boron, aluminum, yttrium, and lanthanum;

x and y are in the mole fractions of z such that when $z=1$ then $x=0.001$ to 0.25, preferably 0.05 to 0.15 and $y=0.001$ to 0.25, preferably 0.002 to 0.20; and q is a number necessary to maintain charge balance with O being oxygen.

In a preferred embodiment, a boron/alkali metal promoted metal oxide catalyst having boron in amounts of about 0.2 to about 20 mole percent (about 0.05 to about 5.0 weight percent), alkali metal promoter selected from the group consisting of lithium, sodium and potassium in amounts of about 0.1 to about 25 mole percent (about 0.1 to about 40 weight percent), metal oxide selected from the group consisting of magnesium oxide, calcium oxide, zinc oxide, and barium oxide are suitable for the catalytic oxidative coupling of aliphatic and alicyclic compounds according to this invention.

DESCRIPTION OF PREFERRED EMBODIMENTS

The process of this invention provides a higher molecular weight hydrocarbon compound by gas phase oxidative coupling of saturated carbon atoms of one aliphatic or alicyclic hydrocarbon compound with a second aliphatic or alicyclic hydrocarbon compound and oxygen in the presence of a mixed basic metal oxide or sulfide catalyst as set forth above, such as a boron-/alkali metal promoted metal oxide catalyst.

Suitable aliphatic and alicyclic hydrocarbon compounds for use as feedstocks in the process of this invention include those compounds having up to eighteen carbon atoms. In the case of aliphatic compounds, $C_1$ through about $C_{18}$ are suitable; $C_1$ through about $C_{12}$ preferred; and $C_1$ through about $C_5$ most preferred. For alicyclic compounds $C_3$ through about $C_{18}$ are suitable and about $C_5$ through about $C_9$ preferred. The limiting factor for use as feedstocks in the process of this invention is that the material be gaseous at reaction conditions of temperature and pressure. Exemplary preferred feedstocks include straight and branched chain saturated and unsaturated aliphatic hydrocarbons, such as methane, ethane, propane, butane, heptane, pentane, hexane, octane, isobutane, isohexane, isooctane, 1-pentene, 1-hexene and mixtures thereof; cyclic chain saturated and unsaturated alicyclic hydrocarbons, such as cyclobutane, cycloheptane, cycloheptene, cyclohexane, cyclohexene and mixtures thereof; and aryl substituted aliphatic and alicyclic hydrocarbons, such as toluene, xylene, mesitylene, durene, cumene and mixtures thereof. The aliphatic and alicyclic hydrocarbon compounds used for oxidative coupling may be the same or different compounds. In the case of unsaturated hydrocarbons, it should be noted that the oxidative coupling of this invention does not occur at the unsaturated bonding. Feedstock gas comprising lower alkanes, principally methane, suitable for use in the process of this invention may comprise any methane containing gas which does not contain interfering compounds. Preferably, methane containing gas when used in the process of this invention comprises about 25 mole percent up to about 100 mole percent methane. Suitable sources of methane containing gas include natural gas, synthetic natural gas (SNG), product gas from gasification of carbonaceous materials, such as gasification of coal, peat, shale, and the like, as well as products of anaerobic digestion of various biomass materials. These gases principally comprise methane and may contain other hydrocarbon gases such as ethane and propane which may produce corresponding chemical reactions to those of methane in the process of this invention. Purification of such mixed gases comprising principally methane is not usually necessary, especially when using the sulfide catalyst which has greater sulfur tolerance. These sources of methane containing gas and processes for producing methane are well known in the art.

Any oxygen containing gas not containing interfering chemical compounds are useful as a feedstock in this invention. The term "oxygen containing gas" as used throughout this disclosure and claims, refers to gas containing oxygen, such as air and gases having an oxygen content of up to 100 percent. It is preferred to use oxygen containing gas comprising over 50 volume percent oxygen. The amount of oxygen used in the process of this invention is expressed as pure oxygen. The oxygen containing gas may be preheated by thermal exchange with the catalyst bed to a temperature suitable for the reaction controlling step of the process.

The reactants are fed to the reaction zone in mole percent proportions of about 80 to about 98 mole percent aliphatic or alicyclic hydrocarbon compounds, preferably about 88 to about 95 mole percent and about 2 to about 20 mole percent oxygen, preferably about 5 to about 12 mole percent. When different aliphatic and alicyclic compounds are used as reactants, they may be used in equal mole proportions or may be used in proportions of about 30 to about 70 mole percent one reactant to further desired reaction. Steam may be added in an amount of up to about 1 mole of steam per mole hydrocarbon to inhibit deep oxidation. Steam does not enter into the reaction but solely acts as an oxidation inhibitor.

The catalyst used in the catalytic process for oxidative coupling of aliphatic and alicyclic compounds according to this invention is a mixed basic metal oxide or sulfide catalyst having the formula xA.yB.zC.qD wherein A, B, C, x, y, z and q have the meanings set forth above with D being oxygen or sulfur. The catalyst used in the process of this invention has only one oxidation state besides the metal, that is Ti, Zr, Hf and Si are only +4 and B, Al, Y and La are only +3, while Mg, Ca, Sr and Ba are only +2 and Li, K, Na, Rb and Cs are only +1. In a preferred embodiment, the catalyst of this invention is a boron/alkali metal promoted metal oxide catalyst having boron in amounts of about 0.2 to about 20 mole percent (about 0.05 to about 5 weight percent) and preferably about 0.4 to about 2 mole percent (about 0.1 to about 0.5 weight percent); alkali metal promoter selected from the group consisting of lithium, sodium and potassium in amounts of about 0.1 to about 25 mole percent (about 0.1 to about 40 weight percent) and preferably about 0.5 to about 8 mole percent (about 0.5 to about 2.0 weight percent) and the remainder metal oxide selected from the group consisting of magnesium oxide, calcium oxide, zinc oxide, and barium oxide. A preferred catalyst is boron/lithium promoted magnesium oxide having about 0.20 to about 0.30 weight percent boron and about 0.8 to about 1.2 weight percent lithium.

The oxide catalyst of this invention may be prepared by mixing water soluble ions and/or compounds of elements set forth as alkali metal (A) and cation (B) to obtain complete solution of the solids. A wide variety of non-interfering ions may be used to form suitable water soluble compounds as long as they do not cause undesired chemical interference. Suitable such compounds include acids, oxides, hydrides, and nitrates, carbonates, hydroxides, respectively. The aqueous solution of (A) and (B) are added to metal oxide (C) powder and well mixed followed by drying at a sufficient temperature and for a sufficient time to expel volatile components. The mixture is then crushed and sieved to a small size for catalytic use. Conventional and well known catalyst manufacturing techniques may be employed to produce the catalyst material noted above. When preparing these catalytic materials, it is preferred to employ manufacturing techniques resulting in a product having a substantially uniform or homogeneous composition. Shaping of the material may be effected according to conventional techniques of the art, particularly tableting, or pelleting or extrusion. The catalyst may be used unsupported or alternatively it may be supported on an inert support as known to the art, such as alumina, silica, activated carbon and the like.

The catalyst may be prepared by mixing a water soluble compound of boron, such as boric acid, boron oxides, borohydrides, and a water soluble salt of the alkali metal promoter, such as nitrate, carbonate, hydroxide or water soluble ion to obtain complete solution of the solids. The aqueous solution of boron and alkali metal is added to the metal oxide powder with stirring to obtain a homogeneous mixture which may then be dried at a temperature in excess of about 110° C. The dried mixture may then be calcined at a temperature of 700° to 750° C. for a sufficient time to expel volatile portions. The mixture is then crushed and sieved to an appropriately small mesh size of about −6 to about +40, preferably about −12 to about +20 for use as a catalyst.

The sulfide catalyst for use in the process of this invention may be prepared by forming a liquid solution of one or two soluble compounds of desired metal or metals and adding it to a metal sulfide powder of the remaining component or components as more fully described in our allowed U.S. patent application 07/359,207, now U.S. Pat. No. 4,945,078 filed May 31, 1989.

The catalyst may be placed into a reactor, such as a tubular fixed bed, fluidized bed, moving bed, or other reactor type known to the art. The reaction of aliphatic and alicyclic compounds with oxygen according to this invention is carried out by passing a gaseous mixture comprising methane and oxygen over the mixed basic metal oxide or sulfide catalyst as defined above at about 300° to about 1100° C., preferably about 600° to about 900° C.. Suitable gas residence times are about 0.002 to about 0.00002 hour preferably about 0.0005 to about 0.0001 hour with space velocity of about 500 to about 50,000 vol/vol/hr, preferably about 1000 to about 5000 vol/vol/hr. The reaction may be carried out at about pressures of about 1 to about 1515 psia, preferably about 0 to about 150 psia. Suitable reactor vessels for use at the above operating temperatures and pressures are well known to the art. The products of the single reactor used in the process of this invention may be passed to a simple separator for separation of the hydrocarbon product, condensate, and vent gas.

The general reaction for oxidative coupling according to this invention may be expressed as:

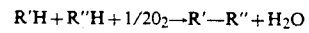

wherein R'H and R"H are each an aliphatic or alicyclic organic hydrocarbon compound which may be the same or different. For example, if both R'H and R"H were ethane, the reaction would be:

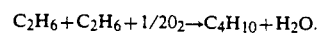

If R'H is propane and R"H is cyclohexane, a major reaction would be:

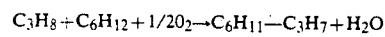

(1-propyl cyclohexane)

The catalyst does not prevent reaction of one compound with itself. Thus, when propane and cyclohexane are both fed to the reaction, propane may react with propane and cyclohexane may react with cyclohexane, but if desired, these reactions may be reduced by adjustment of the propane/cyclohexane feed ratio. In all instances of reaction according to this invention, oxidative coupling provides a process for producing higher molecular weight hydrocarbons.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A process for producing higher molecular weight hydrocarbons by gas phase oxidative coupling of saturated carbon atoms of one aliphatic or alicyclic hydrocarbon compound with a second aliphatic or alicyclic hydrocarbon compound, said process comprising:

oxidative coupling compounds selected from aliphatic hydrocarbon compounds, alicyclic hydrocarbon compounds, and mixtures thereof having up to 18 carbon atoms each to form a higher molecular weight hydrocarbon compound in the presence of oxygen and a mixed basic metal catalyst having the formula:

$xA.yB.zC.qD$ wherein
A is an alkali metal selected from lithium, sodium, potassium, rubidium, cesium and mixtures thereof;
B is selected from the group consisting of;
 a cation which has an ionization state 1 greater than the ionization state of C wherein B is selected from scandium, yttrium, lanthanum, actinium, aluminum, boron, and mixtures thereof, preferably boron, aluminum, yttrium, and lanthanum when C is selected from beryllium, magnesium, calcium, strontium, barium, radium, zinc, cadmium, mercury and mixtures thereof, preferably magnesium, calcium, barium and zinc; and B is selected from titanium, zirconium, hafnium, silicon and mixtures thereof, when C is selected from scandium, yttrium, lanthanum, actinium, aluminum, boron and mixtures thereof, preferably boron, aluminum, yttrium, and lanthanum; and
 a cation which has an ionization state 2 and 3 greater than the ionization state of C wherein B is selected from hafnium, tantalum, niobium, vanadium and mixtures thereof; C is selected from magnesium, calcium, strontium, barium, and mixtures thereof;
D is selected from oxygen, and sulfur;
x and y are in the mole fractions of z such that when $z=1$ then $x=0.001$ to $0.25$, preferably $0.05$ to $0.15$ and $y=0.001$ to $0.25$, preferably $0.002$ to $0.20$; and
q is a number necessary to maintain charge balance with D.

2. A process according to claim 1 wherein said aliphatic and alicyclic hydrocarbon compounds are selected from straight and branched chain saturated and unsaturated aliphatic hydrocarbons, cyclic chain saturated and unsaturated alicyclic hydrocarbons, and aryl substituted aliphatic and alicyclic hydrocarbons wherein said aliphatic compounds have 1 to about 12 and said alicyclic compounds have about 5 to about 9 carbon atoms.

3. A process according to claim 2 wherein said aliphatic hydrocarbon compounds are selected from methane, ethane, propane, butane, heptane, pentane, hexane, octane, isobutane, isohexane, isooctane, 1-pentene, 1-hexene and mixtures thereof.

4. A process according to claim 2 wherein said alicyclic hydrocarbon compounds are selected from cyclobutane, cycloheptane, cycloheptene, cyclohexane, cyclohexene, and mixtures thereof.

5. A process according to claim 2 wherein said aryl substituted aliphatic and alicyclic hydrocarbon compounds are selected from toluene, xylene, mesitylene, durene, cumene and mixtures thereof.

6. A process according to claim 1 wherein B is selected from the group consisting of boron, aluminum, yttrium, lanthanum and mixtures thereof and C is selected from the group consisting of magnesium, calcium, barium, zinc and mixtures thereof 7. A process according to claim 6 wherein $x=0.05$ to $0.15$ and $y=0.03$ to $0.10$.

8. A process according to claim 1 wherein B is selected from the group consisting of silicon, titanium, zirconium, hafnium and mixtures thereof and C is selected from the group consisting of boron, aluminum, yttrium, lanthanum and mixtures thereof.

9. A process according to claim 8 wherein $x=0.05$ to $0.15$ and $y=0.002$ to $0.20$.

10. A process according to claim 1 wherein D is oxygen.

11. A process according to claim 1 wherein D is sulfur.

12. A process according to claim 1 wherein said catalyst is a boron/alkali metal promoted metal oxide, said boron present in about 0.2 to about 20 mole percent, said alkali metal selected from the group consisting of lithium, sodium and potassium and present in about 0.1 to about 25 mole percent, and the balance said metal oxide selected from the group consisting of magnesium oxide, calcium oxide, zinc oxide, barium oxide and mixtures thereof.

13. A process according to claim 12 wherein said boron is present in about 0.4 to about 2 mole percent.

14. A process according to claim 12 wherein said alkali metal is present in about 0.5 to about 8 mole percent.

15. A process according to claim 12 wherein said alkali metal is selected from the group consisting of lithium, sodium, potassium and mixtures thereof.

16. A process according to claim 12 wherein said alkali metal is lithium.

17. A process according to claim 12 wherein said metal oxide is selected from the group consisting of magnesium oxide, calcium oxide, zinc oxide, barium oxide and mixtures thereof.

18. A process according to claim 12 wherein said metal oxide is magnesium oxide.

19. A process according to claim 12 wherein said process is carried out at a temperature of about 300° to about 1100° C.

20. A process according to claim 12 wherein said process is carried out at a temperature of about 600° to about 900° C.

21. A process according to claim 12 wherein said process is carried out at a pressure of about 1 to about 1515 psia.

22. A process according to claim 12 wherein said process is carried out at a pressure of about 1 to about 150 psia.

23. A process according to claim 12 wherein the gas residence time is about 0.002 to about 0.00002 hr.

24. A process according to claim 12 wherein the gas residence time is about 0.0005 to about 0.000 hr.

25. A process according to claim 12 wherein said compound selected from aliphatic hydrocarbon compounds, alicyclic hydrocarbon compounds and mixtures thereof is fed to a reaction zone in about 80 to about 98 mole percent and said oxygen is fed to said reaction zone in about 2 to about 20 mole percent.

26. A process according to claim 12 wherein said compound selected from aliphatic hydrocarbon compounds, alicyclic hydrocarbon compounds and mixtures thereof is fed to a reaction zone in about 88 to about 95 mole percent and said oxygen is fed to said reaction zone in about 5 to about 12 mole percent.

27. A process according to claim 1 wherein said process is carried out at a temperature of about 300° to about 1100° C.

28. A process according to claim 1 wherein said process is carried out at a temperature of about 600° to about 900° C.

29. A process according to claim 1 wherein said process is carried out at a pressure of about 1 to about 1515 psia.

30. A process according to claim 1 wherein said process is carried out at a pressure of about 1 to about 150 psia.

31. A process according to claim 1 wherein the gas residence time is about 0.002 to about 0.0000 hr.

32. A process according to claim 1 wherein the gas residence time is about 0.0005 to about 0.0001 hr.

33. A process according to claim 1 wherein said compound selected from aliphatic hydrocarbon compounds, to a reaction zone in about 80 to about 98 mole percent and said oxygen is fed to said reaction zone in about 2 to about 20 mole percent.

34. A process according to claim 1 wherein said compound selected from aliphatic hydrocarbon compounds, alicyclic hydrocarbon compounds and mixtures thereof is fed to a reaction zone in about 88 to about 95 mole percent and said oxygen is fed to said reaction zone in about 5 to about 12 mole percent.

35. A process according to claim 1 wherein said process is carried out at a temperature of about 300° to about 1100° C., said pressure is about 1 to about 1515 psia, the gas residence time is about 0.002 to about 0.0002 hr, and said compound is selected from aliphatic hydrocarbon compounds, alicyclic hydrocarbon compounds and mixtures thereof is fed to a reaction zone in about 80 to about 98 mole percent and said oxygen is fed to said reaction zone in about 2 to about 20 mole percent.

36. A mixed basic metal oxide catalyst having the formula:

$$xA.yB.zC.qO$$

wherein

A is an alkali metal selected from lithium, sodium, potassium, rubidium and cesium;

B is a cation which has an ionization state 1 greater than the ionization state of C;

B is selected from scandium, yttrium, lanthanum, actinium, aluminum, boron and mixtures thereof when C is selected from beryllium, magnesium, calcium, strontium, barium, radium, zinc, cadmium, mercury and mixtures thereof and B is selected from titanium, zirconium, hafnium, silicon and mixtures thereof when C is selected from scandium, yttrium, lanthanum, actinium, aluminum, boron and mixtures thereof;

x and y are in mole fractions of z such that when $z=1$ then $x=0.002$ to 0.25, and $y=0.001$ to 0.25; and q is a number necessary to maintain charge balance with O being oxygen.

37. A catalyst according to claim 36 wherein $x=0.05$ to 0.15.

38. A catalyst according to claim 36 wherein $y=0.002$ to 0.20.

39. A catalyst according to claim 36 wherein said B is present in about 0.4 to about 2 mole percent.

40. A catalyst according to claim 36 wherein said A is present in about 0.5 to about 8 mole percent.

41. A catalyst according to claim 36 wherein A is lithium.

42. A catalyst according to claim 36 wherein C is magnesium.

43. A catalyst according to claim 36 wherein A is lithium and C is magnesium.

44. A catalyst according to claim 36 wherein said A is present in about 0 5 to about 8 mole percent and said B is present in about 0.4 to about 2 mole percent.

* * * * *